(12) United States Patent
Van Dongen et al.

(10) Patent No.: US 11,058,323 B2
(45) Date of Patent: Jul. 13, 2021

(54) DEVICE AND METHOD FOR ASSESSING RESPIRATORY DATA IN A MONITORED SUBJECT

(71) Applicant: MEDWEAR B.V., Groningen (NL)

(72) Inventors: Jeroen Willem Frans Van Dongen, Loenen aan de Vecht (NL); Johan Oosterheert, Budel (NL)

(*) Notice: Subject to any disclaimer, the term of this patent is extended or adjusted under 35 U.S.C. 154(b) by 652 days.

(21) Appl. No.: 15/515,988

(22) PCT Filed: Oct. 1, 2015

(86) PCT No.: PCT/NL2015/050688
§ 371 (c)(1),
(2) Date: Mar. 30, 2017

(87) PCT Pub. No.: WO2016/053103
PCT Pub. Date: Apr. 7, 2016

(65) Prior Publication Data
US 2017/0231526 A1    Aug. 17, 2017

(30) Foreign Application Priority Data
Oct. 1, 2014  (NL) ...................................... 2013551

(51) Int. Cl.
*A61B 5/091* (2006.01)
*A61B 5/024* (2006.01)
(Continued)

(52) U.S. Cl.
CPC .............. *A61B 5/091* (2013.01); *A61B 5/024* (2013.01); *A61B 5/0806* (2013.01);
(Continued)

(58) Field of Classification Search
CPC ....... A61B 5/091; A61B 5/024; A61B 5/0806; A61B 5/0816; A61B 5/1116; A61B 5/6804
See application file for complete search history.

(56) References Cited

U.S. PATENT DOCUMENTS 5,261,397 A     11/1993  Grunstein
5,546,952 A *   8/1996   Erickson ............... A61B 5/0816
                                                                600/529
(Continued)

OTHER PUBLICATIONS

International Preliminary Report on Patentability, EPO/PCT, including Reply and amendments to claims under Article 19.
(Continued)

*Primary Examiner* — Patrick Fernandes
(74) *Attorney, Agent, or Firm* — Marcus C. Dawes

(57) ABSTRACT

Disclosed is a method and device for assessing respiratory data in a monitored subject. The disclosed method comprises collecting respiratory data of the subject at different levels of exertion with a physiological monitoring system (15-19), the respiratory data at least relating to instantaneous lung volume and comprising the end expiratory lung volume (EELV) after expirations; collecting exertion level data of the subject at the different levels of exertion, the exertion level data at least relating to instantaneous oxygen demand and/or heart rate; establishing a parametric relation (14, 15) between the collected respiratory data and the collected exertion level data, the parametric relation being described by one or more parameters; and assessing the respiratory data of the subject in terms of the value of the one or more parameters. The method and device allow a reliable measuring of dynamic hyperinflation in subjects without requiring much attention on the part of the subject.

12 Claims, 6 Drawing Sheets

(51) Int. Cl.
*A61B 5/08* (2006.01)
*A61B 5/11* (2006.01)
*A61B 5/00* (2006.01)

(52) U.S. Cl.
CPC .......... *A61B 5/0816* (2013.01); *A61B 5/1116* (2013.01); *A61B 5/1118* (2013.01); *A61B 5/6804* (2013.01)

(56) References Cited

U.S. PATENT DOCUMENTS

| | | | |
|---|---|---|---|
| 9,615,773 B1 * | 4/2017 | Kayyali | A61B 5/08 |
| 2004/0215050 A1 * | 10/2004 | Morello | A61M 1/1086 |
| | | | 600/17 |
| 2006/0195149 A1 | 8/2006 | Hopper | |
| 2007/0073168 A1 | 3/2007 | Zhang | |
| 2010/0113893 A1 * | 5/2010 | Cohen | A61B 5/0205 |
| | | | 600/301 |
| 2011/0092795 A1 * | 4/2011 | Derchak | A61B 5/0806 |
| | | | 600/409 |
| 2015/0157275 A1 * | 6/2015 | Swamy | A61B 5/7275 |
| | | | 600/301 |

OTHER PUBLICATIONS

International Search Report, EPO/PCT.
Second International Written Opinion EPO/PCT.

* cited by examiner

DEVICE AND METHOD FOR ASSESSING RESPIRATORY DATA IN A MONITORED SUBJECT

FIELD OF THE INVENTION

The present invention relates to a method and corresponding device for assessing respiratory data in a monitored subject. The invention in particular relates to a method and device for determining pulmonary parameters of individuals, especially pulmonary parameters of patients with obstructive pulmonary diseases. More particularly, this invention provides a method and device for robustly and accurately measuring dynamic hyperinflation in individuals, the method requiring little if any attention of the individual.

BACKGROUND OF THE INVENTION

Individuals with chronic obstructive pulmonary disease (COPD) and other similar diseases may suffer from dyspnea (shortness of breath) and other respiratory discomforts. Due to expiratory flow limitations and/or reduced elasticity of the lungs, air trapping and lung hyperinflation may occur, causing progressive loss of lung volume available for active breathing. Hyperinflation particularly occurs on exertion but may also occur at rest in individuals having such a disease in an advanced stage.

Dynamic hyperinflation is associated with periods of increased drive to breathe, such as occurs during exercise, excitement or in case of pulmonary infections. A patient will have limited time to exhale air and the amount of exhaled air will decrease with respect to the amount of inhaled air in a breathing cycle (a breathing cycle corresponds to one inhalation-exhalation sequence) resulting in hyperinflation. In a state of hyperinflation the amount of air that can additionally be inhaled is limited, resulting in a decrease of lung capacity available for active breathing, seriously hindering patients with COPD and similar diseases in their breathing capacity.

It is clinically important to offer an early diagnosis of individuals that are suspected of suffering, or already suffer from COPD or other lung diseases, since such early diagnosis may result in an earlier treatment and prevent even more problems. Further, known methods such as spirometry for instance require cumbersome procedures and are generally intrusive and unpleasant to a patient.

It is an object of the present invention to provide a method and device for assessing respiratory data in a monitored subject in an accurate and robust manner. A particular object relates to providing a method and device for robustly and accurately measuring dynamic hyperinflation in individuals, the method requiring little if any attention of the individual.

SUMMARY OF THE INVENTION

This and further objects are achieved in accordance with a first aspect of the present invention by a method according to claim 1. The method for assessing respiratory data in a monitored subject comprises:
  collecting respiratory data of the subject at different levels of exertion, the respiratory data at least relating to instantaneous lung volume, and comprising the end expiratory lung volume (EELV) after expirations;
  collecting exertion level data of the subject at the different levels of exertion, the exertion level data at least relating to instantaneous oxygen demand
  establishing a parametric relation between the collected respiratory data and the collected exertion level data, the parametric relation being described by one or more parameters; and
  assessing the respiratory data of the subject in terms of the value of the one or more parameters.

The method in a particular embodiment is able to assess hyperinflation, more preferably dynamic hyperinflation in a patient unremarkably, that is with little, if any, attention from the patient and without hindering the patient. This permits the patient to perform normal daily activities. The method further allows assessing dynamic hyperinflation in a patient in an early stage of disease, typical diseases comprising obstructive pulmonary diseases, such as COPD, chronic bronchitis, emphysema, chronic or acute asthma, and others.

The monitored subject may be a healthy person or a patient, but the invention may also be applied to another animal, such as a mammal.

The parametric relation between the collected respiratory data and the collected exertion level data may in principle be represented by any conceivable mathematical function having one or more parameters. The value of the one or more parameters is determined by fitting the mathematical function to the collected data by known procedures, such as by least square fitting procedures. The inventors have found that parameters obtained by fitting a mathematical function to the relation between the collected respiratory data and the collected exertion level data provide an accurate and sensitive measure of the occurrence of pulmonary diseases, in particular of hyperinflation.

Examples of suitable mathematical functions comprise but are not limited to functions that exhibit a variation between an upper limit and a lower limit of the respiratory data, logarithmic and/or exponential functions, polynomial functions of any degree, such as quadratic functions for instance, and linear functions. In a useful embodiment of the invention, a method is provided wherein the parametric relation between the collected respiratory data and the collected exertion level data is linear, i.e. may be represented by a linear mathematical function. Although other more complex functions may describe the relation between the collected data more accurately, the inventors have established that a linear function is already able to significantly discriminate between healthy subjects and those suffering from some form of (dynamic) hyperinflation.

In such embodiment, a particularly robust assessment of respiratory data is achieved by providing a method wherein the relation is linear and the parameter comprises the gradient of the linear parametric relation. It has been established that such parameter is relatively insensitive to absolute errors in the respiratory data and/or the exertion level data of the subject at the different levels of exertion. This is an advantage since the data mentioned above may be easily influenced by extraneous factors, such as by the specific posture of the individual during monitoring. On the other hand, such parameter has proven to be sensitive to the occurrence of pulmonary diseases, in particular of relatively low levels of dynamic hyperinflation.

The invention relates to a method wherein the respiratory data comprise the instantaneous lung volume. Monitoring instantaneous lung volume involves monitoring the changes in lung volume with time during a certain period of interest, which may be minutes, hours, days or even longer. Typically, lung volume will increase with inhalation and decrease again when exhaling.

According to the invention, the respiratory data comprise the end expiratory lung volume (EELV) after expirations only. These EELV's are readily obtained by selecting the minima in a lung volume versus time recording.

The respiratory data may be obtained by any method known in the art, such as by spirometry. In a particularly useful embodiment however, the respiratory data are obtained by respiratory plethysmography, more preferably by respiratory inductive plethysmography.

Further data required in accordance with the invention comprise exertion level data that at least relate to oxygen demand or need of the monitored subject during exertion. A monitored subject may at least partly fulfil instantaneous oxygen demand by increasing instantaneous heart rate, by increasing breathing frequency or by a combination of both. Monitoring oxygen demand may therefore be adequately carried out by monitoring instantaneous heart rate, which involves monitoring the changes in heart rate that occur with time during a certain period of interest, which again may be minutes, hours, days or even longer. Typically, heart rate may increase with an increasing level of exertion (or oxygen demand) and decrease with decreasing exertion level (or oxygen demand).

An embodiment of the invention provides a method wherein the exertion level data comprise heart rate, as measured by a heart rate measuring device. A suitable heart rate monitor comprises a transmitter attached to a belt that is worn around the chest, and a receiver for collecting the heart rate data. The transmitter receives an electrical signal that is transmitted through the heart muscle in order for it to contract and sends an electromagnetic signal containing heart rate data to the receiver. Other systems are also suitable, including systems using the Doppler Effect.

A particularly useful embodiment of the invention provides a method wherein the exertion level data are obtained from the respiratory data, in particular but not limited to instantaneous lung volume data. Instantaneous lung volume data represent the cyclic changes in lung volume with time due to inhalation and exhalation cycles. The frequency of such breathing cycles will generally depend on the level of exertion, and its frequency may increase with increasing exertion level (or oxygen demand), and decrease again after the level of exertion (or oxygen demand) has been lowered.

The breathing frequency—as measure for exertion—in an embodiment of the invention is obtained from the recorded respiratory data. The breathing frequency can be obtained from these data in several ways, such as by establishing the duration of respiratory cycles. Such duration may for instance be established by measuring the time difference between instants of ends of expiration. The instants of ends of expiration occur at the end of each breathing cycle, defined as a sequence of an inhalation and an exhalation. Other methods for determining the breathing frequency from the recorded respiratory data may also be used, such as establishing the time difference between the starts of breathing cycles, or between other corresponding advents in respiratory cycles. It is also possible in a preferred embodiment of the method to use any kind of averaging technique to obtain a moving average of breathing frequency with time. It is for instance possible to obtain a moving average breathing frequency at a certain time from the preceding n breathing (respiratory) cycles, where n preferably ranges for 2 to 10, more preferably from 3 to 8, most preferably from 4 to 6.

In another embodiment the values for Time of Inspiration (TI) are used. The TI is established by measuring the time difference between instants of ends of expiration and subsequent instants of end of inspiration. The inverse of the TI results in a frequency (=1/TI) which can be used as a measure for exertion. It is also possible in a preferred embodiment of the method to use any kind of averaging technique to obtain a moving average of the frequency with time.

In another embodiment the values for Time of Expiration (TE) are used. The TE is established by measuring the time difference between instants of ends of inspiration and subsequent instants of end of expiration. The inverse of the TE results in a frequency (=1/TE) which can be used as a measure for exertion. It is also possible in a preferred embodiment of the method to use any kind of averaging technique to obtain a moving average of the frequency with time.

The method can in principle be used on individuals in widely differing postures, such as those encountered in sitting, walking, running, bicycling, performing household activities, climbing, and any other conceivable posture. In useful embodiments, the posture of the monitored individual is relatively stable while performing the method, such as encountered in bicycling for instance.

It has advantages to provide yet another embodiment of the invented method, further comprising collecting data related to the posture of the subject. These posture data may be used to correct the respiratory and exertion level data of the subject obtained at different levels of exertion, if appropriate. A useful embodiment comprises a method wherein the posture data comprise instantaneous 3D shape data of the torso of the subject with time.

The invention further relates to a device for assessing respiratory data in a monitored subject, which device is used in conjunction with the invented method. According to one aspect of the invention, the device comprises:

respiration monitoring means for collecting respiratory data of the subject at different levels of exertion, the respiratory data at least relating to instantaneous lung volume and comprising the end expiratory lung volume (EELV) after expirations;

exertion level monitoring means for collecting exertion level data of the subject at the different levels of exertion, the exertion level data at least relating to instantaneous oxygen demand;

establishing a parametric relation between the collected respiratory data and the collected exertion level data, the parametric relation being described by one or more parameters; and assessing the respiratory data of the subject in terms of the value of the one or more parameters.

According to the invention, the computing means of the device are configured to establish a parametric relation between the collected respiratory data and the collected exertion level data, the parametric relation being described by one or more parameters; and assessing the respiratory data of the subject in terms of the value of the one or more parameters. The assessment may comprise comparing the value of the one or more parameters with certain threshold values for these parameters in order to establish a condition of health or a condition of disease, or a state of disease. It will be clear that any method of assessment is available in the context of the present invention.

Several useful embodiments of the invented device are described below, the advantages of which have already been addressed above in the context of the invented method.

In a useful embodiment of the invention, the device further comprises posture monitoring means for collecting posture and/or position data of the subject, especially from, though not necessarily limited to, the torso, as well as computing means for correcting the collected respiratory data, using the posture data.

An embodiment of the device provides computing means for establishing a linear parametric relation between the collected respiratory data and the collected exertion level data.

Yet another embodiment of the device provides computing means for establishing a linear parametric relation between the collected respiratory data and the collected exertion level data wherein the parameter comprises the gradient of the linear parametric relation.

The invention provides a device wherein the respiration monitoring means are configured to collect respiratory data comprising instantaneous lung volume, in particular end expiratory lung volume (EELV) after expirations.

Another embodiment relates to a device wherein the respiration monitoring means comprise respiratory plethysmographic sensors, more preferably respiratory inductive plethysmographic sensors. Such sensors are known per se to one skilled in the art and are commercially available.

Other embodiments of the device relate to the exertion level monitoring means which in one embodiment comprise a heart rate measuring device, and in another particularly useful embodiment comprise the respiration monitoring means configured for collecting the respiratory data of the subject. In the latter embodiment, the exertion level data preferably comprise breathing frequency, obtained from the (moving average) duration of respiration cycles (or parts of respiration cycles, like TI or TE). The duration of any respiration cycle may be obtained in several ways, as was already described above.

Another embodiment of the invention provides a device further comprising posture monitoring means for collecting data related to the posture of the subject, in particular comprising posture monitoring means configured for obtaining instantaneous 3D shape data of the torso of the subject.

In a useful embodiment of the invention, a device is provided wherein the computing means comprise a processor; a computer-readable memory operatively coupled to the processor; wherein the computer-readable memory is adapted to receive the respiratory and/or exertion level data of the subject at different levels of exertion; and wherein the processor is configured to establish the parametric relation between the collected respiratory data and the collected exertion level data, and assess the respiratory data of the subject. A device which is portable by the subject is particularly preferred.

Other useful embodiments of the device comprise a wearable item that carries at least the respiration monitoring means and/or the exertion level monitoring means. Such wearable items may comprise a garment, a shirt, and/or one or more bands, and provide an individual with a comfortable monitoring system that can be used in normal life situations and/or during periods of exercise.

BRIEF DESCRIPTION OF THE DRAWINGS

The present invention will now be described in more detail by reference to the following detailed description of a preferred embodiment of the present invention and the accompanying figures in which.

DETAILED DESCRIPTION OF A PREFERRED EMBODIMENT

Figure 1:
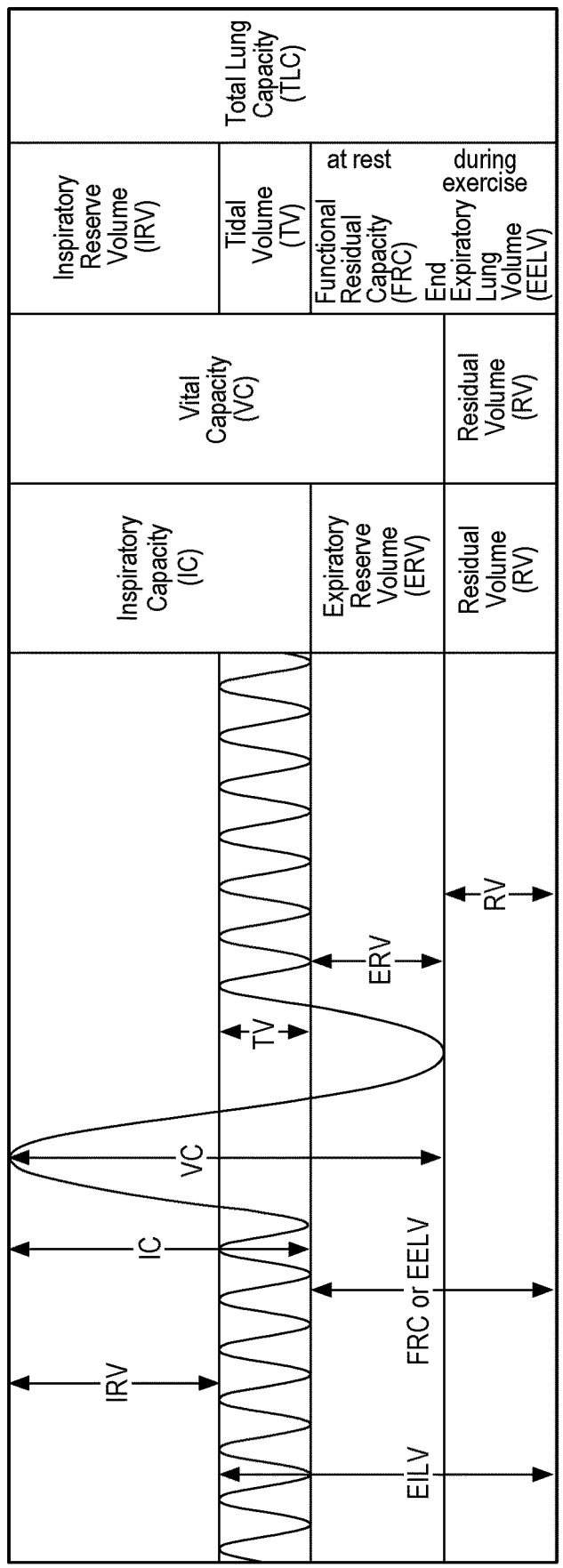
FIG. 1 schematically illustrates the definition of relevant lung volumes to be used in embodiments of the invention.

With reference to FIG. 1, relevant lung volumes to be used in embodiments of the invention are schematically shown. Total lung capacity (TLC) corresponds to the total volume of air the lungs can contain. Vital capacity (VC) is the volume of air breathed out from a maximal inspiration to a maximal expiration (or the inverse) and the residual volume (RV) is the volume of air remaining in the lungs after a maximal expiration effort. The functional residual capacity (FRC) is the volume of air remaining in the lungs after a tidal expiration at rest. Volume names often used during exercise are end inspiratory lung volume (EILV) and end expiratory lung volume (EELV), and the difference of these volumes defines tidal volume (TV). The inspiratory reserve volume (IRV) is the maximal volume that can be inhaled from the end-inspiratory level and the expiratory reserve volume (ERV) is the maximal volume that can be exhaled from the end-expiratory level. The sum of TV and IRV results in the inspiratory capacity (IC) which is the inspiratory volume from a regular expiration up to maximal inspiration, and generally varies in proportion with the EELV.

Figure 2A:
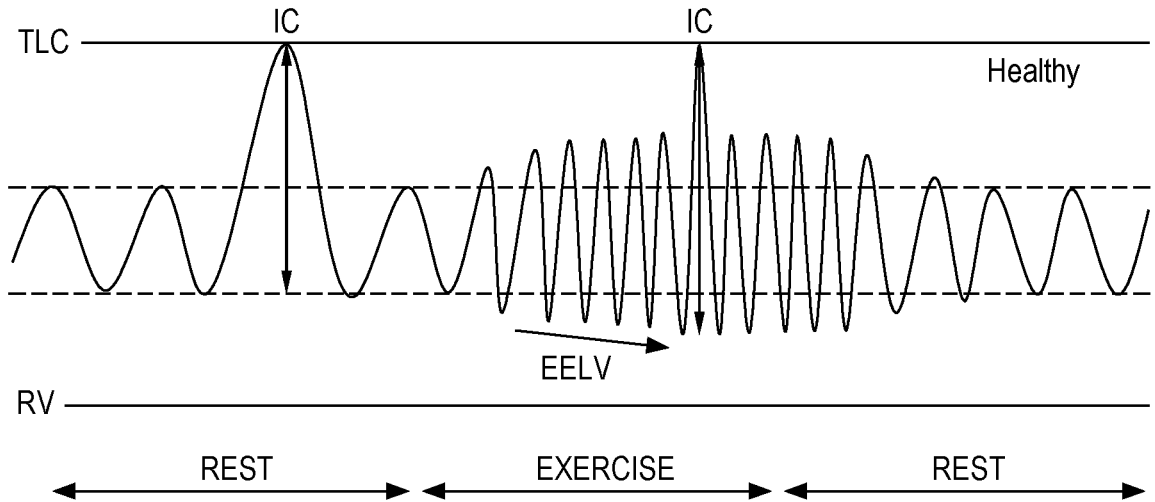
FIG. 2 schematically illustrates lung volume response to exercise for a healthy person and a person suffering from dynamic hyperinflation.

FIG. 2(A) illustrates a normal subject's response (lung volume versus time) to an increased respiratory demand, such as occurs during exertion. The principal response is use IRV and ERV to increase TV, while a secondary response is to increase breathing frequency, in particular at higher levels of respiratory demand. Because normal subjects have substantial IRV and ERV, TV is easily increased. Healthy subjects using their ERV then demonstrate a decreasing EELV—as shown in FIG. 2(A), but the change in EELV may be small. When EELV decreases, IC increases.

Figure 2B:
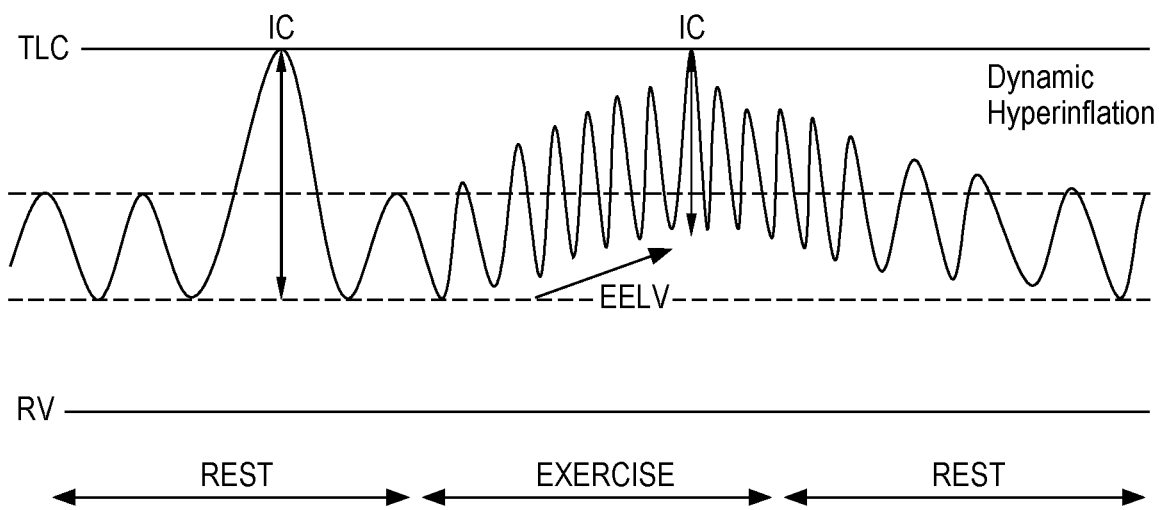

FIG. 2(B) on the other hand schematically illustrates a patient suffering from COPD. The patient's ERV is difficult to exploit due to expiratory flow limitations and incomplete expiration and ERV is not used to increase TV when needed, e.g. during increased activity. Due to repeated incomplete expiration the EELV raises and the patient gets hyperinflated using the IRV without significantly increasing TV. As a result IC decreases and ventilation can only be increased by faster breathing, further worsening hyperinflation and breathing becomes so restricted that the patient has to stop activity. This phenomenon is known as "dynamic hyperinflation". Dynamic hyperinflation is dynamic since lung volumes generally return to their original values after exertion is brought to lower levels again.

Particularly during exercise, COPD patients may experience discomfort such as dyspnea and breathlessness. Furthermore, dynamic hyperinflation can cause even more problems like alveolar overdistention resulting in hypoxemia, hypotension, or alveolar rupture. Being able to track and manage dynamic hyperinflation in COPD patients at an early stage is therefore important.

The invention in one embodiment offers a method for assessing dynamic hyperinflation in a monitored subject. The invented method is based on the discovery that the presence or absence of dynamic hyperinflation and an indication of its degree (volume and/or speed of induction) can be reliably determined by establishing a parametric relation between collected respiratory data and collected exertion level data, the parametric relation being described by one or more parameters, and assessing the degree of dynamic hyperinflation in terms of the value of the one or more parameters.

In a particularly useful embodiment, two parameters turn out to yield a particularly reliable and sensitive prediction or detection of the presence of dynamic hyperinflation. The parameters comprise end expiratory lung volumes (EELV) after expirations and the breathing frequency, obtained by the time difference between instants of ends of expiration. Breathing frequency is indicative of the level of exertion, and is easily obtained from respiratory data.

Figure 4A:
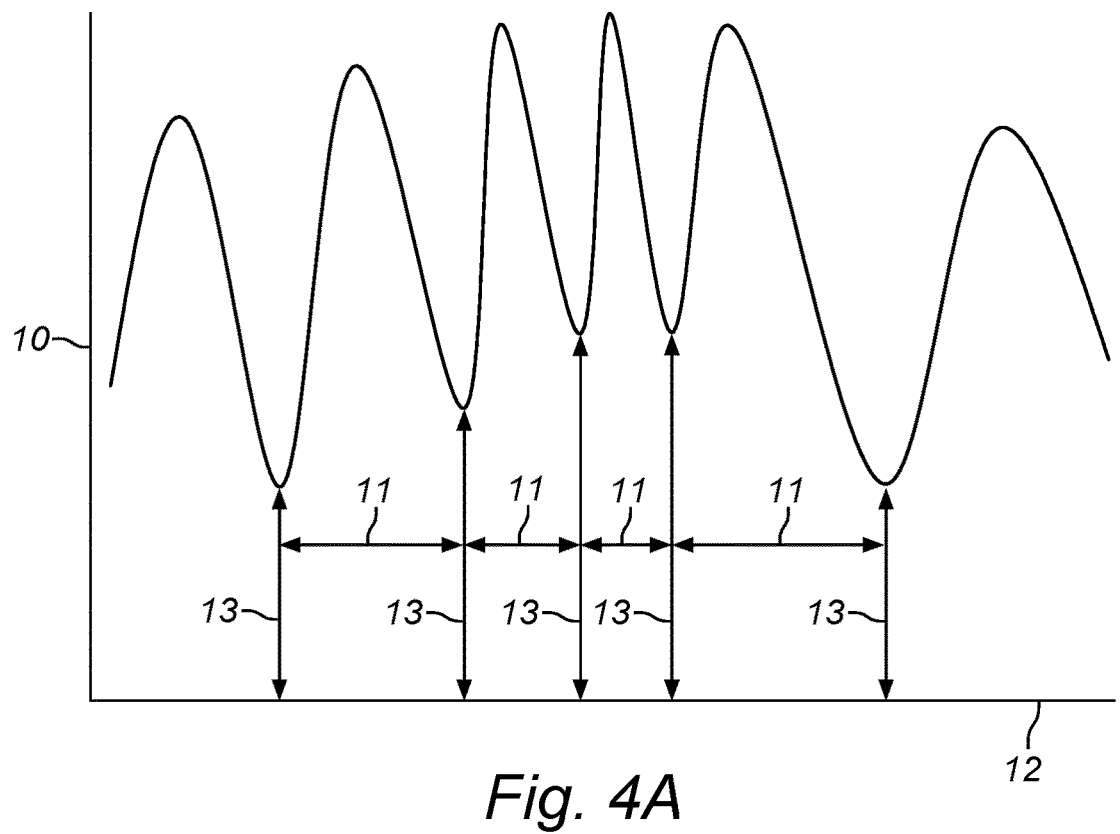
FIGS. 4A and 4B schematically illustrate a graph of lung volume versus time and relevant parameters used in embodiments of the method of the invention.
Figure 6A:
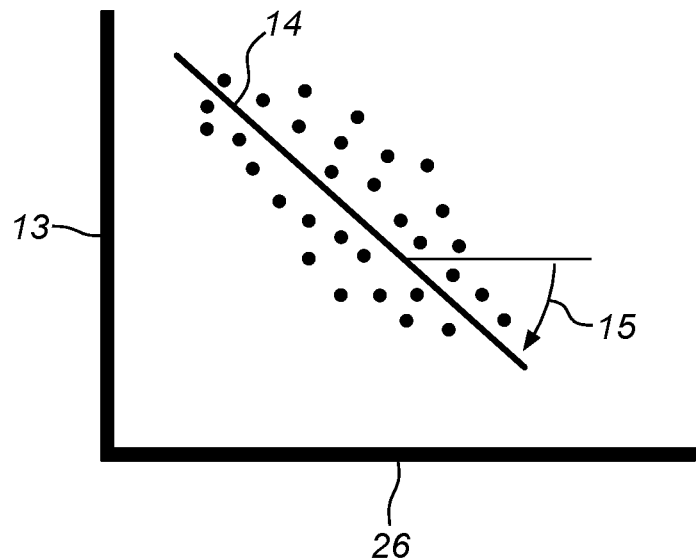
FIGS. 6A and 6B schematically illustrate a parametric relationship that is indicative of the presence or absence of dynamic hyperinflation, as used in an embodiment of the invention.
Figure 6B:
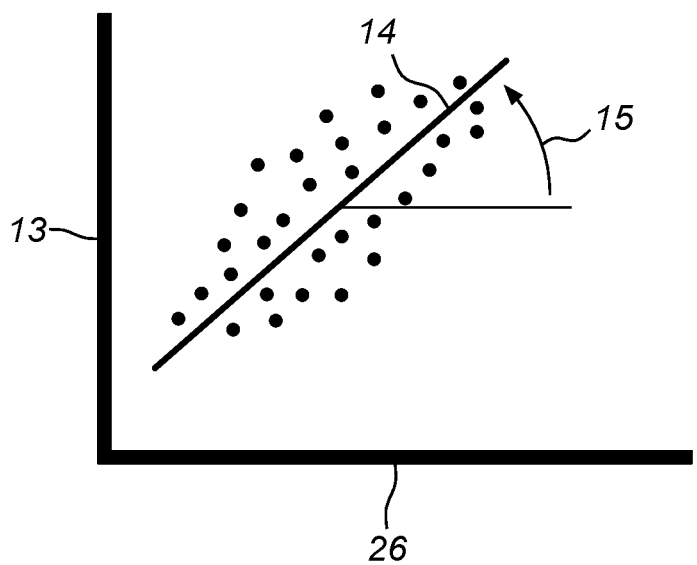

FIG. 4A illustrates exemplary respiratory data. The graph represents the tidal lung volumes 10 (in liter) of a series of breaths versus time 12 (in seconds). Each breath has a rising inspiratory portion and a falling expiratory portion. One inspiration-expiration cycle takes a certain amount of time 11, which may differ from cycle to cycle. Time intervals 11 are usually defined in seconds. The inverse of a time interval 11 for a cycle defines breathing frequency in 1/sec for said cycle. An average breathing frequency of the preceding n cycles may also be used. To each breathing cycle moreover is associated an EELV 13 (the minima between cycles). For each cycle therefore, a unique combination of values of EELV 13 and prior breathing frequency 26 may be calculated from the respiratory data taken during exertion. This results in a collection of data points (26, 13), as shown in FIGS. 6A and 6B. Data points shown on the left in the graphs are indicative of relatively low levels of exertion (low breathing frequencies), while data points shown on the right in the graphs are indicative of relatively high levels of exertion (high breathing frequencies). Instead of breathing frequency, heart rate (at each EELV) can also be used, also in combination with breathing frequency.

Figure 4B:
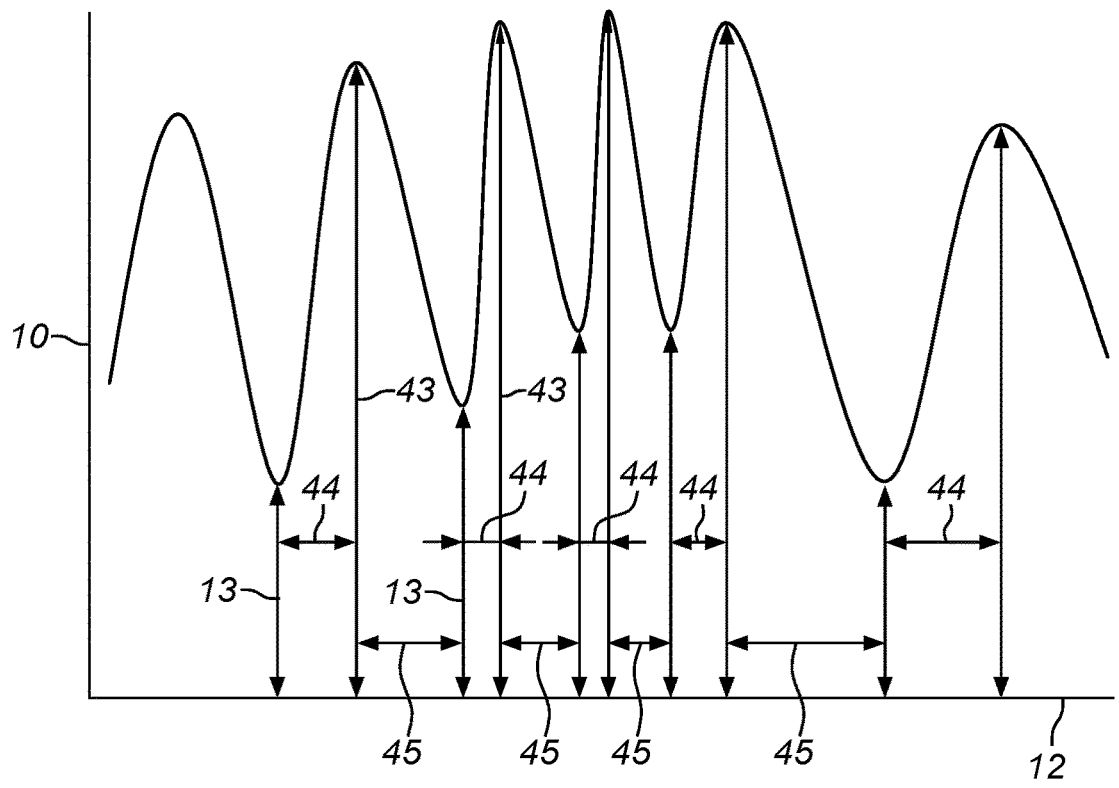

Other embodiments of the method of the invention use parts of respiration cycles such as the Time of inspiration TI and the Time of Expiration TE. FIG. 4B defines the TE and TI for respiratory cycles. The graph represents the tidal lung volumes 10 (in liter) of a series of breaths versus time 12 (in seconds). Each breath has a rising inspiratory portion and a falling expiratory portion. One inspiration takes a certain amount of time 44, which may differ from inspiration to inspiration. Time intervals 44 correspond to the TI and are usually defined in seconds. The TI is established by measuring the time difference 44 between instants of ends of expiration and subsequent instants of end of inspiration. The inverse of the TI defines some kind of inspiration frequency in 1/sec which may be used for data analysis, as described above. One expiration takes a certain amount of time 45, which may differ from expiration to expiration. Time intervals 45 correspond to the TE and are usually defined in seconds. The TE is established by measuring the time difference 45 between instants of ends of inspiration and subsequent instants of end of expiration. The inverse of the TE defines some kind of expiration frequency in 1/sec which may be used for data analysis, as described above.

It turns out that the collected data is very sensitive to the presence or absence of dynamic hyperinflation. FIG. 6A shows a graph obtained on a patient having COPD and associated dynamic hyperinflation, while FIG. 6B is indicative of a healthy person. As shown, the parametric relation between the EELV data 13 and the collected breathing frequencies 26 may be fitted with a linear function 14. Other functions may also be used if appropriate. A particularly sensitive parameter comprises the gradient (or slope) 15 of the linear parametric relation, depicted by line 14. Data obtained at different levels of exertion on a patient having COPD show a negative slope 15 (FIG. 6A), while data obtained at different levels of exertion on a healthy person show a positive slope 15. It should be noted that the slope for a healthy person may also be about zero, but a significantly negative slope turns out to be indicative of (incipient) dynamic hyperinflation.

The present invention may be used in any patient monitoring system as long as respiratory data is available from which at least EELV and breathing frequency can be determined. It is possible to use the method of the invention in a hospital, clinic, or laboratory environment and use data from respiratory sensors available in such environments. Suitable sensors include spirometric measuring systems and body plethysmography arrangements for instance. These however are less portable and may limit or even prevent patient motion. In a preferred embodiment of the invention therefore, the method is practiced in a patient's day-to-day environment while the patient is performing day-to-day activities, or while the patient performs some exercise, such as when cycling for instance. In such embodiments, respiratory sensors are preferably portable and light weight, and are arranged on or incorporated in a wearable item, such as a shirt, jacket, bands, patches, and the like.

Figure 3A:
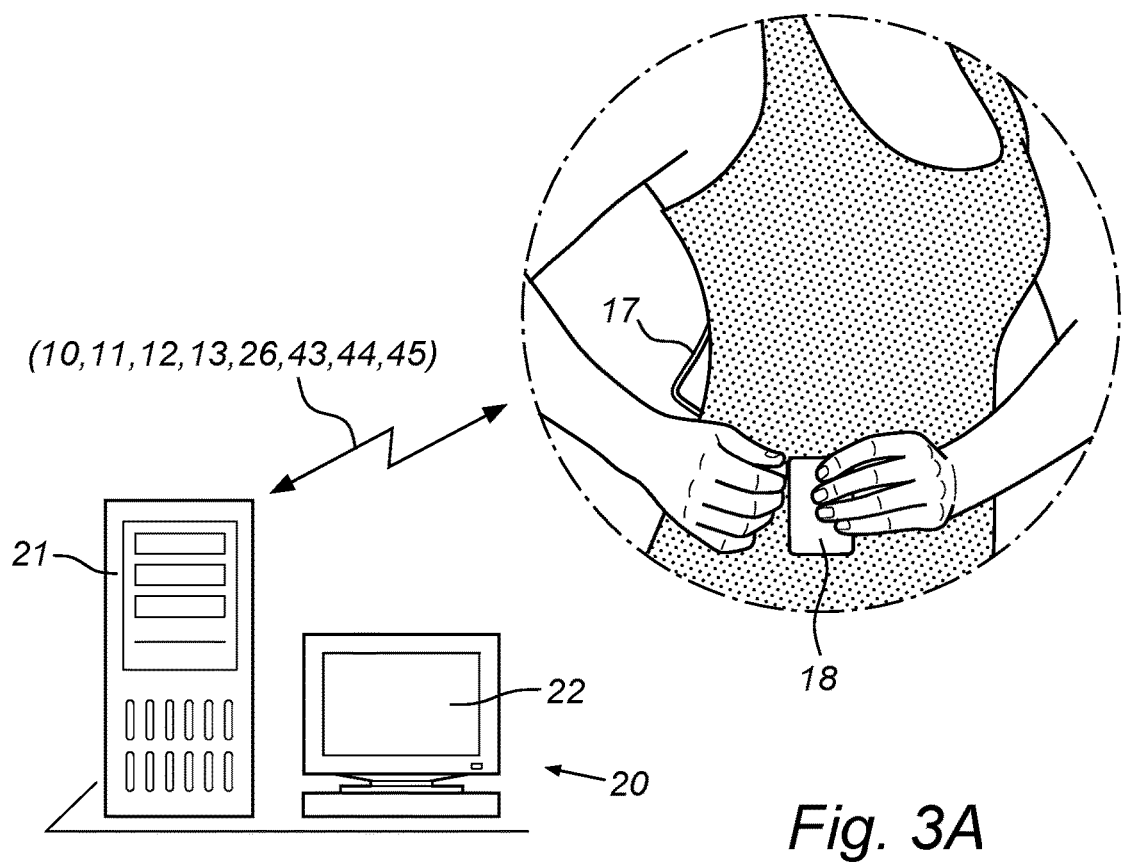
FIGS. 3A and 3B schematically illustrate embodiments of an ambulatory device in accordance with the invention.
Figure 3B:
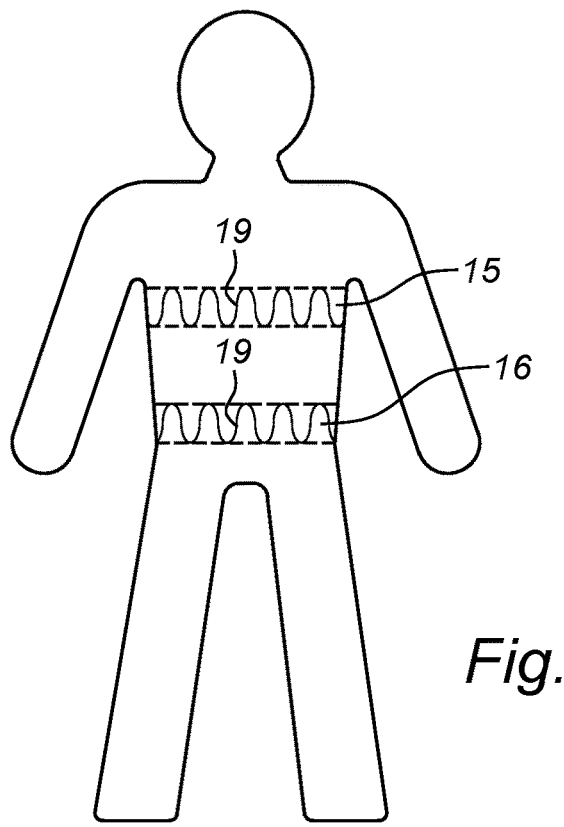

An exemplary embodiment of a shirt provided with monitoring sensors is shown in FIGS. 3A and 3B. The subject of FIG. 3B is provided with two bands (15, 16) that are configured to measure respiratory lung volumes. One band 15 is arranged around the rib cage and produces first signals indicative of instantaneous lung volume. A second band 16 is arranged around the abdomen and produces second signals indicative of instantaneous lung volume. Both signals may be used as such to produce the graphs of FIGS. 6A and 6B, or they may be combined in some way to produce the graphs of FIGS. 6A and 6B, for instance by taking a (weighted) sum of the data produced.

The size sensors 19 incorporated in the bands (15, 16) may be based on technologies known in the art, including magnetometers; strain gauges using magnetic, mechanical or optical means; optical techniques including interferometry; electrical impedance; surface electrical or magnetic activity; body plethysmography, ultrasonic and doppler measurements of body wall motions or body diameters; and so forth. Preferred size sensors are based on respiratory inductive plethysmography (RIP). RIP responds to anatomic size changes by measuring the self-inductance of one or more conductive elements (metallic or non-metallic) arranged in the bands (15, 16) on the body portion to be measured. RIP sensor self-inductance varies with size in response to an underlying body part size change. The changing self-inductance is sensed by a variable frequency oscillator/demodulator module, the output of which is responsive to oscillator frequencies and ultimately to sensor size.

The data that originate from the sensor(s) is transmitted via suitable wiring 17 (see FIG. 3A) to a portable data unit or PDU 18, that is conveniently carried in a small pocket on the shirt. The bands (15, 16) incorporate a size sensor 19 that is sensitive to respiration and may also comprise other sensors (not shown), such as posture sensors, accelerometers, ECG sensors, temperature sensors, and so forth. The PDU 18 stores data and accepts input from the wearer of the shirt. The PDU 18 may also be incorporated in the shirt itself and further retrieves and (wirelessly) transmits sensor data to storage and analysis systems. The PDU 18 may be provided with a processing device for processing sensor data, and/or processed and/or raw data may also be transmitted to a remote computer system 20. As shown in FIG. 3A, a suitable data analysis system 20 comprises a workstation computer 21 with processor to which is connected a monitor 22 for viewing sensor data. Raw or (partly) processed sensor data (10, 11, 12, 13, 26, 43, 44, 45) is transferred to system 20, and stored in computer readable memory for further processing. The processor of computer system 20, or in other embodiments a processor of the PDA, or a processor of any other device, such as a smartphone, is configured to establish a parametric relation between the collected respiratory data and the collected exertion level data, and assess the respiratory data of the subject.

Figure 5:
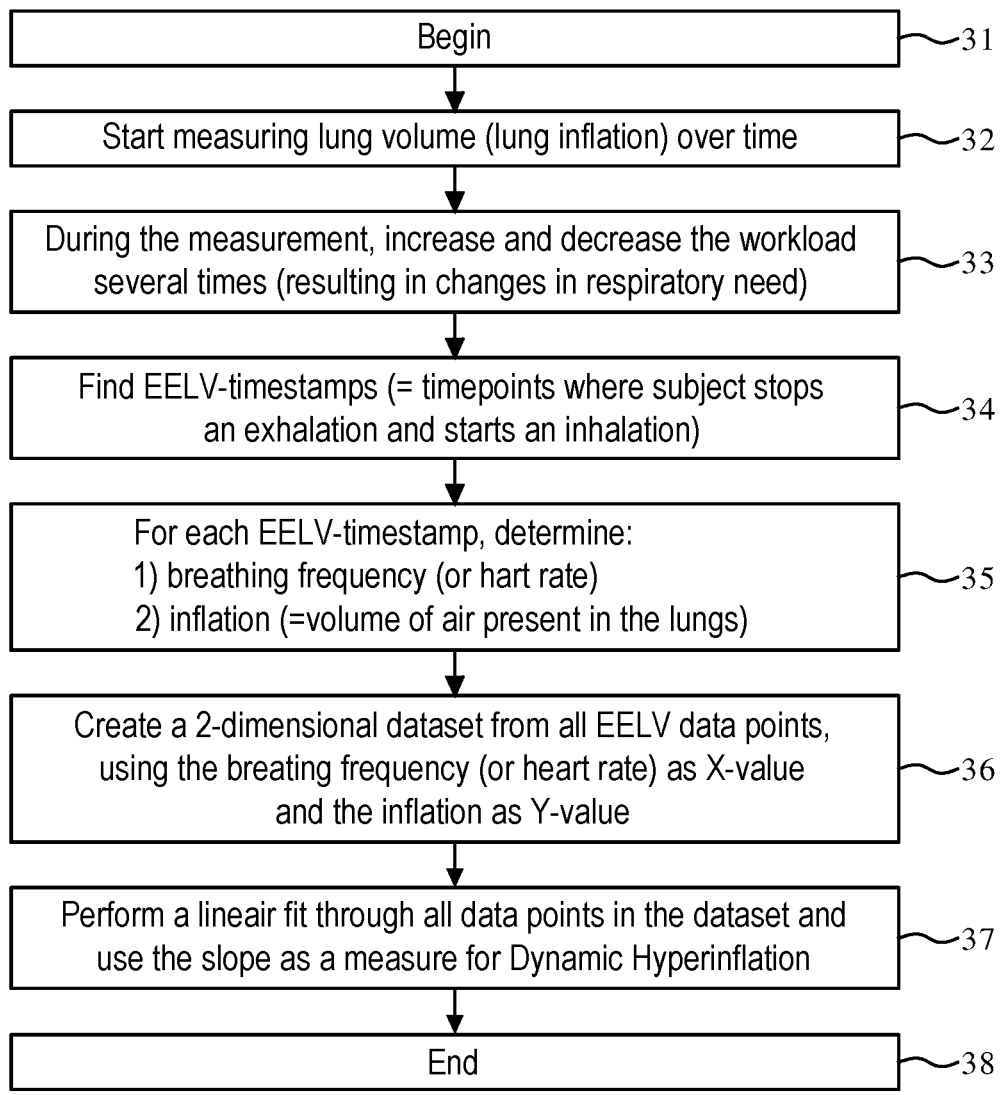
FIG. 5 schematically represents a flow chart of a method in accordance with an embodiment of the invention.

An exemplary flow chart of a programmed method according to an embodiment of the invention is illustrated in FIG. 5. After beginning at step 31, a next step 32 measures lung volumes 10 over a certain time period. This step 32 is performed while decreasing and increasing the workload (or the level of exertion) a number of times in step 33 to obtain a well defined and representative sample of respiratory data for data analysis. The minimum and maximum level of exertion (or breathing frequency 26) required to achieve a representable data sample depends on conditions such as the health of the person involved, the sensors used, and so on. One skilled in the art will readily be able to obtain a representative sample without undue burden. In a next step 34, the processor determines EELV timestamps, defined as the times where the person's exhalation stops and an inhalation starts. The EELV timestamps generally correspond to the instants in time where the lung volume 10 reaches a local minimum. A next step 35 evaluates breathing frequency for each EELV timestamp. This breathing frequency 26 for an EELV timestamp is defined as the inverse of the time expired since the previous EELV timestamp. The average breathing frequency of several preceding breaths can also be used as the breathing frequency for one EELV. The same step 35 also evaluates the EELV 13 (the volume of air present in the lungs at the end of exhalation) for each timestamp. A next step 36 creates a two-dimensional dataset from the computed EELV 13 and corresponding breathing frequency 26 data, the latter being the independent variable in the dataset. In a final step 37, a linear fit is carried out of the collected dataset (13, 26) which produces a gradient or slope 15 of the linear relationship 14. The value of the slope 15 turns out to be highly representative for the occurrence of dynamic hyperinflation. The algorithm ends at step 38.

The invention described herein is not to be limited in scope by the disclosed preferred embodiment, the latter being intended as illustration only of several aspects of the invention. Various modifications of the invention may be made and will become apparent to one skilled in the art from the foregoing description. Such modifications are also intended to fall within the scope of the appended claims.

The invention claimed is:

1. A device for assessing hyperinflation in a monitored subject, the device comprising:
respiration monitoring means for collecting respiratory data of a subject at different levels of exertion, the respiratory data at least relating to instantaneous lung volume and comprising a plurality of end expiratory lung volumes (EELV) after expirations;
exertion level monitoring means for collecting exertion level data of the subject at the different levels of exertion, the exertion level data at least relating to instantaneous oxygen demand and comprising heart rate, as measured by a heart rate measuring device, or breathing frequency obtained from the collected respiratory data; and
computing means configured for
calculating a parametric relation between said respiratory data collected by said respiration monitoring means and said exertion level data collected by said exertion level monitoring means;
determining a value of one or more parameters from said parametric relation; and
assessing a presence of hyperinflation in the subject based on said value of said one or more parameters,
wherein the parametric relation between said collected respiratory data and said collected exertion level data is linear, and wherein the one or more parameters comprises a gradient of the linear parametric relation.

2. The device according to claim 1, where the computer means calculating said parametric relation between said respiratory data and said exertion level data and assessing the presence of hyperinflation in the subject based on the value of said one or more parameters comprises computer means for assessing dynamic hyperinflation in the monitored subject.

3. The device according to claim 1, wherein the computing means configured for determining the value of one or more parameters from the linear parametric relation between said respiratory data and said exertion level data comprises computing means configured for deriving the gradient of the linear parametric relation.

4. The device of claim 1, wherein said respiration monitoring means comprise respiratory plethysmographic sensors, including respiratory inductive plethysmographic sensors.

5. The device according to claim 1, wherein said exertion level monitoring means are configured for collecting a Time of Inspiration (TI), obtained from said respiratory data.

6. The device according to claim 1, where said exertion level monitoring means are configured for collecting a Time of Expiration (TE), obtained from said respiratory data.

7. The device according to claim 1, further comprising posture monitoring means for collecting data related to a posture of said monitored subject.

8. The device according to claim 7, wherein said posture monitoring means collects instantaneous 3D shape data of a torso of said monitored subject.

9. The device according to claim 1, wherein the computing means comprises:
a processor;
a computer-readable memory operatively coupled to said processor;
wherein the computer-readable memory is adapted to receive the respiratory and/or exertion level data of the subject at different levels of exertion; and
wherein the processor is configured to calculate the parametric relation between said respiratory data and said exertion level data, and assess said respiratory data of said subject.

10. The device according to claim 1, wherein said device is portable by said monitored subject.

11. The device according to claim 1, further comprising a wearable item that carries said respiration monitoring means and/or said exertion level monitoring means.

12. The device according to claim 11, wherein said wearable item comprises a garment, a shirt, and/or one or more bands.

\* \* \* \* \*